United States Patent
Braun et al.

(10) Patent No.: US 12,403,088 B2
(45) Date of Patent: *Sep. 2, 2025

(54) OPHTHALMIC COMPOSITIONS AND METHODS FOR REDUCING OXIDATIVE DAMAGE TO AN EYE LENS

(71) Applicant: University of Louisville Research Foundation, Inc., Louisville, KY (US)

(72) Inventors: Ori Braun, Palo Alto, CA (US); Martin G. O'Toole, Louisville, KY (US); Shlomit Schaal, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 434 days.

This patent is subject to a terminal disclaimer.

(21) Appl. No.: 17/849,328

(22) Filed: Jun. 24, 2022

(65) Prior Publication Data

US 2023/0046275 A1    Feb. 16, 2023

Related U.S. Application Data

(63) Continuation of application No. 15/549,280, filed as application No. PCT/US2016/017005 on Feb. 8, 2016, now Pat. No. 11,406,591.

(60) Provisional application No. 62/113,932, filed on Feb. 9, 2015.

(51) Int. Cl.
| | |
|---|---|
| A61K 9/00 | (2006.01) |
| A61K 9/08 | (2006.01) |
| A61K 31/7016 | (2006.01) |
| A61K 47/26 | (2006.01) |
| A61P 27/02 | (2006.01) |

(52) U.S. Cl.
CPC .......... *A61K 9/0048* (2013.01); *A61K 9/0051* (2013.01); *A61K 9/08* (2013.01); *A61K 31/7016* (2013.01); *A61K 47/26* (2013.01); *A61P 27/02* (2018.01)

(58) Field of Classification Search
CPC ...... A61K 9/0048; A61K 9/0051; A61K 9/08; A61K 31/7016; A61K 47/26; A61P 27/02
See application file for complete search history.

(56) References Cited

U.S. PATENT DOCUMENTS

| | | | |
|---|---|---|---|
| 4,778,815 A | 10/1988 | Cash | |
| 5,422,376 A | 6/1995 | Webb | |
| 5,626,863 A | 5/1997 | Hubbell et al. | |
| 5,767,105 A | 6/1998 | Peyman | |
| 5,785,993 A | 7/1998 | Baker et al. | |
| 5,801,033 A | 9/1998 | Hubbell et al. | |
| 5,804,597 A | 9/1998 | Yamakoshi et al. | |
| 5,876,438 A | 3/1999 | Kelleher | |
| 6,060,582 A | 5/2000 | Hubbell et al. | |
| 6,121,341 A | 9/2000 | Sawhney | |
| 6,149,931 A | 11/2000 | Schwartz et al. | |
| 6,306,922 B1 | 10/2001 | Hubbell et al. | |
| 6,387,977 B1 | 5/2002 | Sawhney et al. | |
| 6,399,655 B1 | 6/2002 | de Juan, Jr. | |
| 6,433,007 B1 | 8/2002 | Gamer et al. | |
| 6,475,508 B1 | 11/2002 | Schwartz et al. | |
| 6,555,526 B2 | 4/2003 | Matsuo et al. | |
| 6,602,975 B2 | 8/2003 | Hubbell et al. | |
| 6,780,427 B2 | 8/2004 | Baker et al. | |
| 7,238,364 B2 | 7/2007 | Sawhney et al. | |
| 7,589,107 B2 | 9/2009 | Matier et al. | |
| 7,727,544 B2 | 6/2010 | Schwartz et al. | |
| 7,732,425 B2 | 6/2010 | Matsuo et al. | |
| 7,906,136 B2 | 3/2011 | Wong et al. | |
| 7,976,833 B2 | 7/2011 | Soli | |
| 8,389,014 B2 | 3/2013 | Longo et al. | |
| 8,741,871 B2 | 6/2014 | Nishizawa et al. | |
| 8,784,897 B2 | 7/2014 | Archambeau et al. | |
| 8,962,684 B2 | 2/2015 | Tojo et al. | |
| 2002/0192289 A1 | 12/2002 | Zheng et al. | |
| 2003/0087985 A1 | 5/2003 | Hubbell et al. | |
| 2003/0223957 A1 | 12/2003 | Schwartz et al. | |
| 2004/0033274 A1 | 2/2004 | Hong et al. | |
| 2004/0086479 A1 | 5/2004 | Grinstaff et al. | |
| 2004/0131582 A1 | 7/2004 | Grinstaff et al. | |
| 2004/0138329 A1 | 7/2004 | Hubbell et al. | |

(Continued)

FOREIGN PATENT DOCUMENTS

| | | |
|---|---|---|
| CN | 101401791 | 4/2000 |
| EP | 1192947 | 4/2002 |

(Continued)

OTHER PUBLICATIONS

"Frequently asked questions about how science works"; Understanding Science How Science Really Work; downloaded online on May 16, 2021. (Year: 2012) https://undsci.berkeley.edu/faqs.php.

Abdelkadar, J. et al. (2014) "Age-Related Cataract and Drug Therapy: Opportunities and Challenges for Topical Antioxidant Delivery to the Lens," *Journal of Pharmacy and Pharmacology*.

Aragona, P. et al. (2014) "Protective Effects of Trehalose on the Corneal Epithelial Cells," *Scientific World Journal* 2014:717835 doi: 10.1155/2015/717835.

Attanasio, F. et al. (2007) "Trehalose Effects on -α-Crystallin Aggregates," *Biochemical and Biophysical Research Communications* 354:899-905.

(Continued)

*Primary Examiner* — Aradhana Sasan
(74) *Attorney, Agent, or Firm* — Khin K. Chin; BOZICEVIC, FIELD & FRANCIS LLP

(57) ABSTRACT

Methods of reducing oxidative damage to an eye of a subject are provided. Aspects of the method include intravitreal injection an antioxidant composition consisting essentially of a non-reducing sugar or a hydrate thereof. In some embodiments, the non-reducing sugar is trehalose. The methods can further include surgical removal of at least a portion of the subject's vitreous humor during a vitrectomy. Also provided are ophthalmic compositions, kits and preloaded injection devices for use in vitrectomy surgery which find use in the subject methods.

8 Claims, 2 Drawing Sheets

(56) References Cited

U.S. PATENT DOCUMENTS

| | | |
|---|---|---|
| 2004/0229814 A1 | 11/2004 | Dillon |
| 2005/0271590 A1 | 12/2005 | Schwartz et al. |
| 2006/0052340 A1 | 3/2006 | Tsuzuki et al. |
| 2006/0057215 A1 | 3/2006 | Raiche |
| 2006/0257391 A1 | 11/2006 | Bartels et al. |
| 2008/0008698 A1 | 1/2008 | Bartels et al. |
| 2008/0132444 A1 | 6/2008 | Li |
| 2009/0048188 A1 | 2/2009 | Matsuo et al. |
| 2009/0170789 A1 | 7/2009 | Gitlin |
| 2010/0297193 A1 | 11/2010 | Archambeau et al. |
| 2011/0033540 A1 | 2/2011 | Daniloff et al. |
| 2011/0054441 A1 | 3/2011 | Erickson et al. |
| 2011/0136935 A1 | 6/2011 | Khor et al. |
| 2011/0166247 A1 | 7/2011 | Myung et al. |
| 2011/0182968 A1 | 7/2011 | Myung et al. |
| 2011/0243883 A1 | 10/2011 | Grinstaff et al. |
| 2012/0082730 A1 | 4/2012 | Banerjee et al. |
| 2012/0189667 A1 | 7/2012 | Boutros |
| 2013/0317457 A1 | 11/2013 | Schmitt |
| 2013/0331458 A1 | 12/2013 | Miyano et al. |
| 2014/0018316 A1 | 1/2014 | Matsuo et al. |
| 2014/0031542 A1 | 1/2014 | Chen |
| 2014/0099375 A1 | 4/2014 | Archambeau et al. |
| 2014/0377838 A1 | 12/2014 | Maynard et al. |
| 2015/0010634 A1 | 1/2015 | Knappe et al. |
| 2015/0290230 A1 | 10/2015 | Tezel et al. |

FOREIGN PATENT DOCUMENTS

| | | |
|---|---|---|
| EP | 1782795 | 5/2007 |
| JP | H09235233 | 9/1997 |
| JP | 2005104970 | 4/2005 |
| WO | WO 198700196 | 1/1987 |
| WO | WO 2008700196 | 1/1987 |
| WO | WO 199317669 | 9/1993 |
| WO | WO 199724129 | 7/1997 |
| WO | WO 200037066 | 6/2000 |
| WO | WO 2003080091 | 10/2003 |
| WO | WO 2004050795 | 6/2004 |
| WO | WO 2005048920 | 6/2005 |
| WO | WO 2011135400 | 11/2011 |
| WO | WO 2013046059 | 4/2013 |
| WO | WO 2014066658 | 5/2014 |
| WO | WO 2014081969 | 5/2014 |

OTHER PUBLICATIONS

Ayranci, E. et al. (2003) "A Method for the Measurement of the Oxygen Permeability and the Development of Edible Films to Reduce the Rate of Oxidative Reactions in Fresh Foods," *Food Chemistry* 80:423-431.

Barbazetto, et al. (2004) "Oxygen Tension in the Rabbit Lens and Vitreous before and after Vitrectomy". Exp Eye Res, 78(5); pp. 917-924.

Baudouin, C. et al. (2013) "Role of Hyperosmolarity in the Pathogenesis and Management of Dry Eye Disease: Proceedings of the Ocean Group Meeting," *Ocul Surf.* 11(4):246-58.

Beebe, D.C. et al. (2011) "Vitreoretinal Influences on Lens Function and Cataract," *Philos Trans R Soc Lond B Biol Sci* 366(1568):1293-300.

Beebe, David C. (2010) "Oxidative Damage and the Prevention of Age-Related Cataracts," *Ophthalmic Research* 44:155-165.

Buerk, D.G. et al. (1993) "$O_2$ Gradients and Countercurrent Exchange in the Cat Vitreous Humor near Retinal Arterioles and Venules," *Microvascular Research* 45, 134-148.

Buwalda, S. et al. (2011) "Self-Assembly and Photo-Cross-Linking of Eight-Armed PEG-PTMC Star Block Copolymers," Biomacromolecules 12:2746-2754.

Cai, M. et al. (2014) "Mitochondria-Targeted Antioxidant Peptide SS31 Protects Cultured Human Lens Epithelial Cells Against Oxidative Stress," *Current Eye Research* 1-8.

Cao, S. et al. (2014) "Prevention of Selenite-Induced Cataratogenesis by Ginkgo Biloba Extract (Egb761) in Wistar Rats," *Current Eye Research* pp. 1-6.

Cejkova, J. (2010) "Reduced UVB-Induced Corneal Damage Caused By Reactive Oxygen and Nitrogen Species and Decreased Changes in Corneal Optics after Trehalose Treatment," *Histol. Histopathol.* 25:1403-1416.

Cejkova, J. (2011) "Favorable Effects of Trehalose on the Development of UVE-Mediated Antioxidant/Pro-Oxidant Imbalance in the Corneal Epithelium, Proinflammatory Cytokine and Matic Metalloproteinase Induction, and Heat Shock Protein 709 Expression," *Graefes Arch. Clin. Exp. Ophthalmol.* 249:1185-1194.

Charles, P.T. et al. (2009) "Reduction of Non-Specific Protein Absorption Using Poly(Ethylene) Glycol (Peg) Modified Polyacrylate Hydrogels in Immunoassays for Staphylococcal Enterotoxin B Detection," *Sensors* 9(1):645-55.

Chen, M. (2014) "Epigallocatechin Gallate Eye Drops Protect Against Ultraviolet B-Induced Corneal Oxidative Damage in Mice," *Molecular Vision* 20:153-162.

Chen, W. et al. (2009) "Trehalose Protects against Ocular Surface Disorders in Experimental Murine Dry Eye Through Suppression f Apoptosis," *Exp Eye Res* 89:311-318.

De Moura, M.R. et al. (2008) "Properties of Novel Hydroxypropyl Methylcellulose Films Containing Chitosan Nanoparticles," *Journal of Food Science* 73(7):N31-7.

Emanuele, E. et al. (2014) "Protective Effect of Trehalose-Loaded Liposomes Against UVB-Induced Photodamage in Human Keratinocytes," *Biomedical Reports* 2:755-759.

European Patent Office, Extended European Search Report issued in corresponding Application No. EP13857463, mailed Jun. 8, 2016.

European Patent Office, First Examination Report issued in corresponding Application No. EP16749665, mailed Feb. 28, 2020.

European Patent Office, Supplementary European Search Report issued in corresponding Application No. EP16749665, mailed Oct. 23, 2018.

Geraldine, P. et al. (2006) "Prevention of Selenite-Induced Cataractogenesis by Acetyl-L-Carnitine: An Experimental Study," *Exp Eye Res* 83(6):1340-49.

Grama, C. et al. (2013) "Efficacy of Biodegradable Curcumin Nanoparticles in Delaying Cataract in Diabetic Rat Model," *PLos One* 8(10):3e78271 doi: 10.1371/journal.pone.0078217.

Gross, N. et al. (2013) "Choroidal Neovascularization Reduced by Targeted Drug Delivery with Cationic Liposome-Encapsulated Paclitaxel or Targeted Photodynamic Therapy with Verteporfin Encapsulated in Cationic Liposomes," *Mol Vos.* 19:54-61.

Hammond, B. et al. (2014) "Oxidative Photodegradation of Ocular Tissues: Beneficial Effects of Filtering and Exogenous Antioxidants," *Experimental Eye Research* 129:135-150.

Hayashi, K. et al. (2004) "Posterior Capsule Opacifaction after Implantation of a Hydrogel Intraocular Lens," *Br J Ophthalmol* 88:182-185.

He, Q. et al. (2014) "Trehalose Alleviates PC12 Neuronal Death Mediated by Lipopolysaccharide-Stimulated BV02 Cells Via Inhibiting Nuclear Transcription Factor NF-KB and AP-1 Activation," *Neurotox Res.* 26(4):430-9. Coi: 10.1007/s12640-014-9487-7.

Hermans, K. et al. (2014) "Cytotoxicity and Anti-Inflammatory Activity of Cyclosporine A Loaded PLGA Nanoparticles for Ocular Use," *Pharmazie* 69(1):32-7.

Hill-Bator, A. et al. (2014) "Trehalose-Based Eye Drops Preserve Viability and Functionality of Cultured Human Corneal Epithelial Cells During Desiccation," *Biomed Res Int* 2014-292138 doi: 10.1155/2014/292139.

Hillel, A. et al. (2011) "Photoactivated Composite Biomaterial for Soft Tissue Restoration in Rodents and in Humans," Science Translational Medicine 3(93) 1-14.

Hill-West, J. et al. (1994) "Inhibition of Thrombosis and Intimal Thickening by in situ Photopolymerization of This Hydrogel Barriers," *Proc. Natl. Acad. Sci. USA* 91:5967-5971.

Holekamp, N. et al. (2005) "Vitrectomy Surgery Increases Oxygen Exposure to the Lens: A Possible Mechanism for Nuclear Cataract Formation," American Journal of Ophthalmology 139(2):302-310.

Hovakimyan, M. et al. (2012) "Evaluation of Protective Effects of Trehalose on Desiccation of Epithelial Cells in Three-Dimensional Reconstructed Human Corneal Epithelium," *Current Eye Research* 37(11):982-989.

(56) References Cited

OTHER PUBLICATIONS

International Search Report issued in corresponding Application No. PCT/US2016/017005, mailed Apr. 19, 2016.
Islam, M.N. et al. (2011) "Eye Diseases-Treatment and Prevention with Antioxidants," *Medicine Today* vol. 23, No. 02:103-105.
Johnson, L.M. et al. (2010) "Formation of Three-Dimensional Hydrogel Multilayers Using Enzyme-Mediated Redox Chain Reaction Initiation," *ACS Appl Mater Interfaces* 2(7):1963-72.
Kan, E. et al. (2015) "Effects of Two Antioxidants: A-Lipoic Acid and Fisetin Against Diabetic Cataract in Mice," *Int. Ophthalmol* 35:115-120.
Kawata, T. et al. (2014) "Glass Transition Temperature of Dried Lens Tissue Pretreated with Trehalose, Maltose, or Cyclic Tetrasaccharide," *SpringerPlus* 3:317.
Kleinberg, TT et al. (2011) "Vitreous Substitutes: A Comprehensive Review," *Surv Ophthalmol* 56(4):300-23.
Li, J. et al. (2012) "Therapeutic Efficacy of Trehalose Eye Drops for Treatment of Murine Dry Eye Induced by an Intelligently Controlled Environmental System," *Mol Vis* 18:317-29.
Liesegang, Thomas (1990) "Viscoelastic Substances in Ophthalmology" *Survey of Ophthalmology* 34(4):268-293.
Lin, S. et al. (2011) "Influence of Physical Properties of Biomaterials on Cellular Behavior," *Pharm Res.* 28(6):1422-30.
Luo, Y. et al. (2008) "Trehalose: Protector of Antioxidant Enzymes or Reactive Oxygen Species Scavenger Under Heat Stress?" *Environmental and Experimental Botany* 63:378-384.
Luyckx, J. et al. (2011) "Trehalose: An Intriguing Disaccharide with Potential for Medical Application in Ophthalmology," *Clinical Ophthalmology* 5:577-581.
Mann, B. et al. (2001) "Smooth Muscle Cell Growth in Photopolymerized Hydrogels with Cell Adhesive and Proteolytically Degradable Domains: Synthetic ECM Analogs for Tissue Engineering," *Biomaterials* 22:3045-3051.
Matsuo, T. (2005) "Cyclic Tetrasaccharide Delays Cataract Formation in the Lens in Vitro," *Cell Preservation Technology* 3(4):238-243.
Matsuo, T. et al. (2002) "Trehalose Eye Drops in the Treatment of Dry Eye Syndrome," *Ophthalmology* 109(11):2024-2029.
Matsuo, T. et al. (2004) "Trehalose Versus Hyaluronan or Cellulose in Eyedrops for the Treatment of Dry Eye," *Jpn. J. Ophthalmol.* J48:321-327.
Nakamura, T. (2008) "The Use of Trehalose-Treated Freeze-Dried Amniotic Membrane for Ocular Surface Reconstruction," *Biomaterials* 29:3729-3737.
Ouasti, S. et al. (2011) "Properties of Novel Hydroxypropyl Methylcellulose Films Containing Chitosan Nanoparticles," *Journal of Food Science* 73(7):N31-37.
Park, Y.D. et al. (2003) "Photopolymerized Hyaluronic Acid-Based Hydrogels and Interpenetrating Networks," *Biomaterials* 24(6):893-900.
Pekel, N. (2004) "Radiation Crosslinking of Biodegradable Hydroxypropylmethylcellulose," *Carbohydrate Polymers* 55(2):139-147.
Porter, A. et al. (2011) "Biomimetic Hydrogels with VEGF Induce Angiogenic Processes in Both hUVEC and hMEC," *Biomacromolecules* 12:242-246.
Priya, R. et al. (2014) "Virulence, Speciation and Antibiotic Susceptibility of Ocular Coagualase Negative Staphylococci CoNS," *J Clin Diagn Res* 8(5):DC33-7 doi: 10-7860/JCDR/2014/7867.4395.
Sabnis, A. et al. (2008) "Cytocompatibility Studies of an in situ Photopolymerized Thermoresponsive Hydrogel Nanoparticle System Using Human Aortic Smooth Muscle Cells," *Journal of Biomedical Materials Research Part A* 52-59.
Sheu, S. et al. (2013) "Resveratrol Stimulates Mitochondrial Bioenergetics to Protect Retinal Pigment Epithelial Cells from Oxidative Damage," *IOVS* 54(9):6426-6438.
Shin, S. et al. (2003) "Preparation and Evaluation of Bioadhesive Benzocaine Gels for Enhanced Local Anesthetic Effects," *International Journal of Pharmaceutics* 260:77-81.
Shui, Y. et al. (2006) "Oxygen Distribution in the Rabbit Eye and Oxygen Consumption by the Lens," *Investigative Ophthalmology & Visual Science* 47(4):1571-1580.
State Intellectual Property Office of China (SIPO), First Office Action issued in corresponding Application No. 201380071008.0 mailed Jun. 24, 2016.
Stefansson, E. (2009) "Physiology of Vitreous Surgery," *Graefes Arch Clin Exp Ophthalmol* 247:147-163.
Sunkireddy, P. et al. (2013) "Natural Antioxidant Biomolecules Promises RFuture Nanomedicine Based Therapy for CataraCT," *Colloids and Surfaces B-Biointerfaces* 112:554-562.
Takeuchi, K. et al. (2010) "Inhibitory Effects of Trehalose on Fibroblast Proliferation and Implications for Ocular Surgery," *Exp Eye Res* 91(5):567-77 doi: 10.1016/j.exer.2010.07.002.
Thassu et al. (2012) "Ocular Drug Delivery Systems: Barriers and Application of Nanoparticulate Systems," *CRC Press*, p. 404.
Wang, Y. et al. (2004) "Effects of the Chemical Structure and the Surface Properties of Polymeric Biomaterials on Their Biocompatibility," *Pharmaceutical Research* 21(8):1362-1373.
Wieland et al. (2007) "Non-Viral Vector Delivery from PEG," *Hyaluronic Acid Hydrogels* 120(3):233-41.
Wikstrom, J. et al. (2012) "Viability of Freeze Dried Microencapsulated Human Retinal Pigment Epithelial Cells," *Eur J Pharm* 47(2):520-526.
Williams, C. et al. (2005) Variable Cytocompatibility of Six Cell Lines with Photoinitiators used for Polymerizing Hydrogels and Cell Encapsulation,: *Biomaterials* 26:1211-1218.
Yasui, T., et al. (2011) "Characterization of Low Viscosity Polymer Solutions for Microchip Electrophoresis of Non-Denatured Proteins on Plastic Chips"; *Biomicrofluidics*, 5(4); 44114-44114-9.

OPHTHALMIC COMPOSITIONS AND METHODS FOR REDUCING OXIDATIVE DAMAGE TO AN EYE LENS

CROSS-REFERENCE TO RELATED APPLICATIONS

This application is a continuation application of U.S. Application Ser. No. 15/549,280, filed Aug. 7, 2017, now U.S. Pat. No. 11,406,591 which is a 371 of International Patent Application No. PCT/US2016/017005 which pursuant to 35 U.S.C. § 119 (e), this application claims priority to the filing date of the U.S. Provisional Patent Application Ser. No. 62/113,932, filed Feb. 9, 2015; the disclosure of which is herein incorporated by reference.

INTRODUCTION

The lens of the eye is a biconvex transparent structure that helps to focus light onto the retina, where mature fiber cells of the lens contain high amounts of protein and are important for the transparency and refractive power of the lens. Normally, these proteins are protected from oxidation by reducing substances and by the low-oxygen environment around the lens. Indeed, within the eye, oxygen concentration decreases sharply from the retina towards the lens due to the presence of the vitreous gel. Surgical removal or involutional degeneration of the vitreous gel often increases the exposure of the lens to oxygen originating from the retinal vasculature. Vitrectomy surgery, or removal of the vitreous humor, is an exponentially growing surgical technique for the treatment of common vitreo-retinal pathologies, including retinal detachments and macular holes, and can lead to increased risk of cataracts. Cataracts (a clouding of an eye lens) are the most common cause of vision loss in people over age 40 and is the principal cause of blindness in the world. In fact, there are more cases of cataracts worldwide than there are of glaucoma, macular degeneration and diabetic retinopathy combined.

Many antioxidant-containing compositions such as intra-operative irrigation solution, topical drops, and oral antioxidants have been developed to attempt to combat the oxidative stress that follows a vitrectomy. Nevertheless, the functionality of those prior compositions has been limited by the fact that the prior compositions had an effectiveness that was short in duration (e.g., minutes) or were entirely ineffective in preventing cataracts and lens opacities.

Tezel et al. (WO2014/081969) disclose polymeric compositions for reducing oxidative damage to the eye of a subject, where the compositions include several components such as a combination of polymeric components (e.g., a viscoelastic polymer and an initiator) and an antioxidant. The polymeric components and initiator are combined and polymerized to take the form of an inter-penetrating cross-linked polymer for use in the eye of surgical patients to remove gas bubbles.

SUMMARY

Methods of reducing oxidative damage to an eye of a subject are provided. Aspects of the method include intra-vitreal injection of an ophthalmic composition consisting essentially of a non-reducing sugar or a hydrate thereof. In some embodiments, the non-reducing sugar is trehalose. The methods can further include surgical removal of at least a portion of the subject's vitreous humor during a vitrectomy. Aspects of the disclosure include ophthalmic compositions for use in reducing oxidative damage to an eye of a subject. Aspects of the disclosure include use of a non-reducing sugar and/or ophthalmic compositions including the same for the manufacture of a medicament for reducing oxidative damage to an eye of a subject. Also provided are ophthalmic compositions, kits and pre-loaded injection devices for use in vitrectomy surgery which find use in the subject methods.

DEFINITIONS

Figure 1:
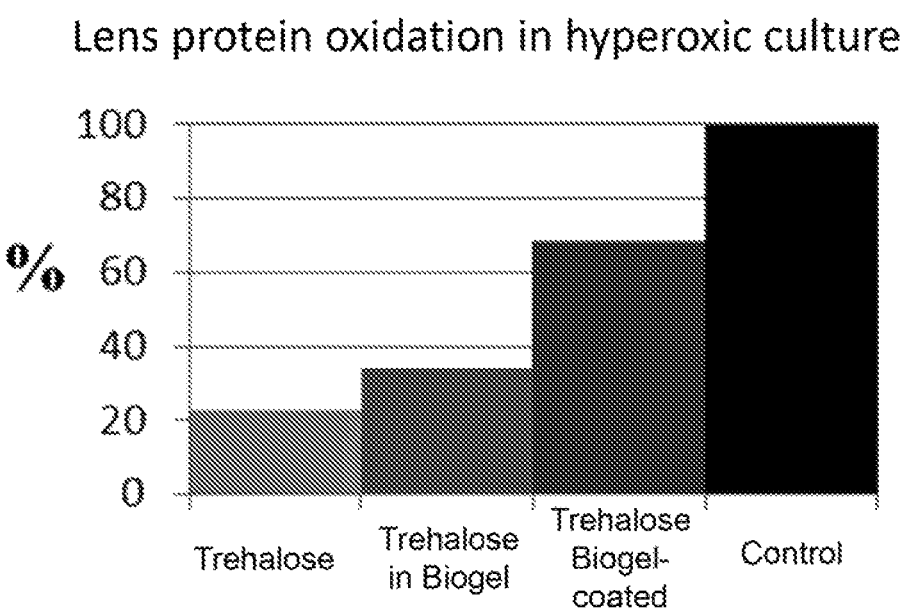
FIG. 1 illustrates that administration of three trehalose-containing compositions to the eye lens in an ex vivo model resulted in a reduced an amount of protein oxidation in the lens, and indicates that trehalose and other non-reducing sugars are useful in protecting an eye lens from oxidative damage.

Unless defined otherwise, all technical and scientific terms used herein have the same meaning as is commonly understood by one of skill in the art to which the invention(s) belong.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

As used herein, the term "solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

The term "pharmaceutically acceptable salt" means a salt which is acceptable for administration to a subject, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

With respect to the antioxidant compositions used in accordance with the presently-disclosed subject matter, the term "antioxidant" is used herein to refer to substances capable of inhibiting oxidation of molecules or, in other words, substances capable of inhibiting the transfer of electrons or hydrogen from a particular substance to an oxidizing agent. In some embodiments, the term "antioxidant" can thus be used interchangeably with the term "oxygen quenching substance."

As used herein, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

"Cataract" refers to an eye condition that includes the clouding or opacity of an eye lens which causes vision loss in a subject. The term "opacity" refers to a condition of lacking transparency, or a condition of opaqueness, e.g., in a part of an eye.

DETAILED DESCRIPTION

As summarized above, methods of reducing oxidative damage to an eye of a subject are provided. Aspects of the method include intravitreal injection of an ophthalmic antioxidant composition consisting essentially of a non-reducing sugar or a hydrate thereof. In some embodiments, the non-reducing sugar is trehalose. Also provided are ophthalmic compositions, kits and pre-loaded injection devices for use in vitrectomy surgery which find use in the subject methods.

Before the present invention is described in greater detail, it is to be understood that this invention is not limited to particular embodiments described, as such may, of course, vary. The invention encompasses various alternatives, modifications, and equivalents, as will be appreciated by those of skill in the art. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Ophthalmic Compositions

The presently-disclosed subject matter is based, at least in part, on the discovery that an ophthalmic composition including a non-reducing sugar can be applied, e.g., intravitreally, to the eye of a subject as an option for reducing damage to the eye (e.g., to the eye lens) that occurs as a result of vitreous removal or vitreous degeneration in the eye, e.g., oxidative damage and/or damage caused by exposure of the eye lens to oxygen. The degeneration of the vitreous gel can occur naturally in subjects of advancing age, and can also be related to, or accelerated by, e.g., a prior surgery, an eye disease or condition or an eye trauma. Vitreous removal can occur during an eye trauma or during vitrectomy eye surgery in the treatment of various eye disorders.

The inventors discovered that the subject non-reducing sugar compositions can prevent damage to the eye, including the eye lens which contains high amounts of protein that are important for the transparency and refractive power of the lens. The trehalose in the subject compositions can have a stabilizing effect in vivo on these endogenous proteins in the eye lens to prevent damage. In some cases, the stabilizing effect of the trehalose is to protect the proteins in the eye lens against stresses, such as desiccation, osmotic shock or heat and to prevent undesirable processes such as protein aggregation. In addition, trehalose can have a direct antioxidant effect in vivo by eliminating reactive oxygen species.

Aspects of the present disclosure include methods of preventing or treating vitreous degeneration in the eye of a subject. The subject may be at risk of vitreous degeneration (e.g., 50 years or older, such as 60 years or older or 70 years or older) where the subject methods are performed to prevent or reduce the occurrence of oxidative damage, or the subject may already be experiencing vitreous degeneration and the methods are performed to treat the resulting oxidative damage. In some cases, prior to treatment according to the subject methods, the subject is assessed for vitreous degeneration.

Aspects of the present disclosure include methods of preventing or treating oxidative damage associated with vitreous removal from the eye of a subject. Vitrectomy refers to the surgical removal of some or all of the vitreous gel from the eye and is performed to treat a number of eye disorders, including diabetic eye disease. Despite the usefulness of vitrectomies in treating various eye disorders, however, the removal of the vitreous gel also routinely results in the formation of cataracts, e.g., during the early post-operative period or during the late post-operative period. In particular, during the early post-operative period, prolonged contact of gas bubbles with the posterior lens surface can result in the lens surface being exposed to an increased amount of oxygen that, in turn, can cause damage to the lens. During the late post-operative period, such exposure to oxygen results in oxidative stress, which can further damage the lens of the eye. Depending on the nature of the eye surgery and condition being treated by the surgery, the eye lens can become cloudy and develop a cataract months or even years after the surgery. In this regard, the present disclosure provides methods, compositions, devices and kits that find use in the attenuation of such oxidative stress and can provide a means to reduce cataract formation and lens opacity following a vitrectomy.

The presently-disclosed subject matter is based, at least in part, on the discovery that an ophthalmic composition including principally a non-reducing sugar can be applied to the eye of a subject as an option for reducing oxidative damage to the eye, including the eye lens of a patient, and in some cases a vitrectomy patient. In some embodiments, the presently-disclosed subject matter thus includes antioxidant compositions and methods for reducing oxidative damage. In particular, the presently-disclosed subject matter includes antioxidant compositions and methods for reducing oxidative damage that make use of a non-reducing sugar for protecting an eye from oxidative damage, e.g., damage that appears post-vitrectomy. The incorporation of an antioxidant, such as a particular non-reducing sugar, into a subject ophthalmic composition used in accordance with the subject methods provides for neutralization of reactive oxygen species and reduction in oxidative damage to the eye.

Aspects of the present disclosure include ophthalmic compositions for use in the subject methods, compositions, devices and kits. As used herein, the term "ophthalmic" refers to a composition which finds use in the treatment of conditions associated with the eye. Applicants discovered that a simple composition based principally on an antioxidant component (e.g. a non-reducing sugar component) can be effective at reducing the occurrence of cataracts post-vitrectomy surgery. The present disclosure provides compositions which lack several of the components (e.g., polymeric components) required by other ophthalmic compositions to provide for a particular function or activity. As such, in some cases, the subject composition consists essentially of an antioxidant (e.g., a non-reducing sugar) in a pharmaceutically acceptable solution.

Any convenient non-reducing sugars can be utilized in the subject compositions. As used herein, the term "non-reducing sugar" refers to a carbohydrate that lacks an aldehyde or ketone group, or a functional equivalent thereof (e.g., a hemiacetal or hemiketal group) and is not oxidized by a weak oxidizing agent (an oxidizing agent that oxidizes aldehydes but not alcohols, such as the Tollen's reagent) in basic aqueous solution or capable of causing reduction of other compounds. In this regard, one characteristic property of non-reducing sugars is that, in basic aqueous medium, non-reducing sugars do not generate any compounds containing an aldehyde group (see, e.g., sucrose, which contains neither a hemiacetal group nor a hemiketal group and, therefore, is stable in water). A reducing sugar refers to any sugar that includes a free aldehyde or ketone group, or functional equivalent thereof (e.g., a hemiacetal or hemiketal group) and is capable of acting as a reducing agent. In general, monosaccharides are reducing sugars. For example, glucose may be present in an open-chain aldehyde containing form which is capable of being oxidized (i.e., is a reducing agent). It is understood that any convenient derivatives, salts or solvates of the subject non-reducing sugars may be utilized in the compositions. Unless indicated otherwise, the term "non-reducing sugar" is meant to include derivatives thereof, salts thereof and solvates (e.g., hydrates) thereof (e.g., as described herein).

The non-reducing sugar can include any convenient number of sugar monomeric units. In some case, the non-reducing sugar is a disaccharide, a trisaccharide or a tetrasaccharide. Any convenient sugar oligosaccharides can be utilized. The non-reducing sugar can be an oligosaccharide of 5 or more units, such as 10 or more, 20 or more, 30 or more, 40 or more, 50 or more, 100 or more, 200 or more, or even more non-reducing sugar units. The size of the oligosaccharide can be selected to provide for a subject composition having a desirable viscosity and injectability for intravitreal injection. The oligosaccharides can be branched or linear. In some embodiments, the non-reducing sugar is a disaccharide such as, in some embodiments, trehalose. In some instances, the non-reducing sugar is sucrose. In certain instances, the non-reducing sugar is trehalose. α,α-1,1-Trehalose is an alpha-linked disaccharide including two α-glucose units linked by an α,α-1,1-glucoside bond. The structure including the 1-1 alpha glucoside bond makes α,α-1,1-trehalose resistant to hydrolysis and stable in solution, e.g., at high temperature and under acidic conditions. Unless otherwise indicated, as used herein, the terms "trehalose", "D-trehalose", "α,α-1,1-trehalose" and "α,α-trehalose" are used interchangeably to refer to the α,α-1,1-form of trehalose.

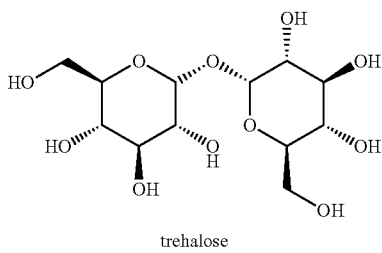

trehalose

In certain instances, the non-reducing sugar is an isomeric form of trehalose, such as α, β-trehalose, also termed neotrehalose or β, β-trehalose, also termed isotrehalose, or a hydrate thereof. In certain instances, the non-reducing sugar is a trehalose oligosaccharide. As used herein, the term "trehalose oligosaccharide" refers to an oligosaccharide (e.g., a trisaccharide or tetrasaccharide) that includes trehalose as the base component with one, two or more optional additional sugars attached to it. In some cases, a trehalose oligosaccharide is the disaccharide trehalose. Any convenient sugars (e.g., monosaccharides or disaccharides) may be utilized in the subject trehalose oligosaccharides, including but not limited to, Glc, Galf, Gal, LGal, Man, All, LAll, Gul, Lido, Tal, Ribf, Rib, Araf, Ara, LAraf, Lara, Xyl, Lyx, and the like. In some instances, the trehalose oligosaccharide is selected from Glcα1-4Trehalose, Glcβ1-6Trehalose, Glcβ1-6Glcβ1-6Trehalose, Galα1-6Galα1-6Trehalose, and a trehalose with an α1-6Gal on one of its glucose residues and an α1-4Glc on the other glucose residue. Unless indicated otherwise, all monosaccharide codes described herein have their standard meaning. For example, Glc refers to D-glucose and Gal refers to D-galactose. In some instances, the non-reducing sugar is a sucrose oligosaccharide. In some cases, a trehalose oligosaccharide is an oligosaccharide including 5 or more units, such as 10 or more, 20 or more, 30 or more, 40 or more, 50 or more, 100 or more, 200 or more, or even more non-reducing sugar units containing trehalose.

As used herein, the term "sucrose oligosaccharide" refers to an oligosaccharide (e.g., a trisaccharide or tetrasaccharide) that includes sucrose as the base component with one or two or more optional additional sugars attached to it. In some cases, a sucrose oligosaccharide is the disaccharide sucrose. Any convenient sugars (e.g., monosaccharides or disaccharides) may be utilized in the subject sucrose oligosaccharides, including but not limited to, Glc, Galf, Gal, LGal, Man, All, LAll, Gul, Lido, Tal, Ribf, Rib, Araf, Ara, LAraf, Lara, Xyl, Lyx, and the like. In certain instances, the sucrose oligosaccharide is selected from raffinose (Galα1-6Sucrose) and stachyose (Galα1-6Galα1-6Sucrose). In some cases, a sucrose oligosaccharide is an oligosaccharide including 5 or more units, such as 10 or more, 20 or more, 30 or more, 40 or more, 50 or more, 100 or more, 200 or more, or even more non-reducing sugar units containing sucrose.

Non-reducing sugars of interest which find use in the subject compositions include, but are not limited to, sucrose, trehalose, raffinose, stachyose, Glcα1-4Trehalose, Glcβ1-6Trehalose, Glcβ1-6Glcβ1-6Trehalose, Galα1-6Galα1-6Trehalose, a trehalose with an α1-6Gal on one of its glucose residues and an α1-4Glc on the other glucose residue, derivatives thereof, salts thereof and hydrates thereof.

Derivatives of non-reducing sugars that find use in the subject compositions include, but are not limited to, phosphorylated sugars, acylated sugars. Any of the non-reducing sugars described herein can be utilized in a phosphorylated derivative form, e.g., where any convenient hydroxyl group of the sugar (e.g., R—OH) is substituted with a phosphoryl group (e.g., R—O—PO$_3^{2-}$). In certain instances, the non-reducing sugar is trehalose 6-phosphate. Any of the non-reducing sugars described herein can be utilized in an acylated derivative form, e.g., where any convenient hydroxyl group of the sugar (e.g., R—OH) is substituted with an acyl group (e.g., R—O—COR', where R' is, in some cases, an alkyl (e.g., methyl or long chain lipiphilic group) or a substituted alkyl). The acyl group(s) can be included via derivatization of any convenient hydroxyl positions of the non-reducing sugar, e.g., at one, two or three of the 2, 3, 6 and 6' positions of trehalose. In certain instances, the non-reducing sugar derivative is an acetylated trehalose. In certain instances, the non-reducing sugar derivative is a trehalose lipid, such as a trehalose including a fatty acid acyl group at the 6' and/or 6' positions, e.g., a C16-C20 fatty acid acyl group. The non-reducing sugar may be utilized in an anhydrous form. However, also included are solvate forms of the non-reducing sugars described herein. In some instances, the composition includes a hydrate form of the non-reducing sugar, such as a monohydrate or a dihydrate form of any of the non-reducing sugars (e.g., or a derivative and/or salt form thereof), described herein. In certain cases, the composition includes D-trehalose dihydrate. In certain cases, the composition includes anhydrous D-trehalose.

In some instances, the subject compositions includes a mixture of two or more non-reducing sugars described herein, such as 2, 3, 4, 5 or 6 non-reducing sugars. Any convenient combinations of the non-reducing sugars described herein may be utilized in the subject compositions. In certain instances, the compositions includes trehalose or a hydrate thereof and at least one additional non-reducing sugar or a derivative, salt or hydrate thereof (e.g., as described herein). In certain embodiments, the composition includes an antioxidant composition composed of a mixture of the non-reducing sugar and an additional antioxidant agent. The additional antioxidant agent which can be used in combination with the subject non-reducing sugar can be selected from nicotinamide, alpha tocopherol, N-acetylcysteine and ascorbic acid. In certain embodiments, the non-reducing sugar component of the subject composition can be replaced with a particular antioxidant. In certain cases, the subject composition includes an equivalent amount of nicotinamide, alpha tocopherol, N-acetylcysteine or ascorbic acid instead of the non-reducing sugar.

In some embodiments, the antioxidant (e.g., non-reducing sugar) component that is included in the compositions is in a powder form, a particulate form, or a combination thereof. The non-reducing sugar component of the composition may be present in a powder or particulate form. In some cases, the powder form of the non-reducing sugar is amorphous. In certain cases, the particular non-reducing sugar that is used in preparation of the subject composition is engineered (e.g., via a spray drying procedure) to have a particular microparticulate form, such as spherical microparticles. Such particles can be described by their geometric diameter. The particles of the non-reducing sugar can be prepared using any convenient methods. It is understood that, depending on the method of preparation, the non-reducing sugar component can include other substances in addition to the non-reducing sugar, such as a surfactant. A particulate non-reducing sugar component for use in the subject compositions can be prepared using any convenient spray drying procedure. A variety of spray drying methods for preparing microparticles of thermally sensitive materials can be adapted for use in the preparation of a particulate non-reducing sugar component having a desired particle size (e.g., diameter) and particle size distribution, including but not limited to, the methods of particle engineering and characterization that are described by Vehring ("Pharmaceutical Particle Engineering via Spray Drying", Pharm Res. 2008 May; 25(5): 999-1022).

In certain cases, the composition includes a non-reducing sugar component that is composed of particles of the sugar having a desirable median diameter (e.g., as described herein). In certain cases, the particulate non-reducing sugar component includes only spherical microparticles and/or sub-micron particles of the non-reducing sugar (e.g., trehalose or a hydrate thereof). The term microparticle is meant to encompass particles that have a size (e.g., diameter) in the micron range and particles having an even smaller size (i.e., sub-micron), and combinations thereof. In some instances, the particulate non-reducing sugar component can further include a powder form of the non-reducing sugar. In certain cases, the powder form has a higher surface area than the particulate form and provides for a faster release profile of the non-reducing sugar as it dissolves in situ. The ratio of powder to particulate in a combination non-reducing sugar component can be selected to provide for a desired release profile of the sugar from the composition. The particles can provide for a desirable extended release profile of the non-reducing sugar from the particles as it dissolves into a surrounding aqueous environment, e.g., in situ in the eye. The diameter of the particles can also be selected to be of a sufficient size to prevent passage of the particles through pores in the ciliary body of the eye. As such, once delivered intravitreally, the particles are substantially retained in the eye.

In some embodiments, the particles of the non-reducing sugar component that are present in the composition have a median diameter in the range of 100 to 2000 nm, such as 100 to 1500 nm, 100 to 1000 nm, 100 to 900 nm, 100 to 800 nm, 100 to 700 nm, 100 to 600 nm, 100 to 500 nm, or 100 to 400 nm; or such as 200 to 2000 nm, 300 to 2000 nm, 400 to 2000 nm, 500 to 2000 nm, 600 to 2000 nm, 700 to 2000 nm, 800 to 2000 nm, 900 to 2000 nm, 1000 to 2000 nm, or 1500 to 2000 nm. In certain instances, the particles of the non-reducing sugar component that are present in the composition have a median diameter in the range of 100 to 1000 nm, such as 200 to 900 nm, 300 to 800 nm, 400 to 800 nm, 450 to 750 nm, 500 to 700 nm, or 550 to 650 nm. In certain instances, the particles of the non-reducing sugar component that are present in the composition have a median diameter of 600±200 nm. In certain instances, the particulate non-reducing sugar component is trehalose or a hydrate thereof.

In some embodiments, the particles of the non-reducing sugar component that are present in the composition have a mean diameter in the range of 100 to 2000 nm, such as 100 to 1500 nm, 100 to 1000 nm, 100 to 900 nm, 100 to 800 nm, 100 to 700 nm, 100 to 600 nm, 100 to 500 nm, or 100 to 400 nm; or such as 200 to 2000 nm, 300 to 2000 nm, 400 to 2000 nm, 500 to 2000 nm, 600 to 2000 nm, 700 to 2000 nm, 800 to 2000 nm, 900 to 2000 nm, 1000 to 2000 nm, or 1500 to 2000 nm. In certain instances, the particles of the non-reducing sugar component that are present in the composition have a mean diameter in the range of 100 to 1000 nm, such as 200 to 900 nm, 300 to 800 nm, 400 to 800 nm, 450 to 750 nm, 500 to 700 nm, or 550 to 650 nm. In certain instances, the particles of the non-reducing sugar component that are present in the composition have a mean diameter of 600±200 nm. In certain instances, the particulate non-reducing sugar component is trehalose or a hydrate thereof.

Particle size distribution can be characterized by the mean diameter and standard deviation (SD) of the particle diameter distribution. In some instances, the particles have a size distribution characterized by a mean diameter in the range of 300 to 800 nm and a SD of 100 to 300 nm, such as about 800 nm±about 200 nm (mean±1SD), about 700 nm±about 200 nm, about 600 nm±about 200 nm, about 500 nm±about 200 nm, about 400 nm±about 200 nm, or about 300 nm±about 200 nm. In certain instances, the particulate non-reducing sugar component is trehalose or a hydrate thereof.

In certain embodiments, the compositions can comprise trehalose (or a hydrate thereof) particles having a diameter of about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm.

An effective amount of the non-reducing sugar can be included in the composition to provide for the desired effect. In some embodiments, the composition comprises 1% to 30% by weight of the non-reducing sugar, such as 1% to 25%, 1% to 20%, 1% to 15%, 1% to 10%, 2% to 10%, 3% to 10%, 4% to 10%, or 5% to 10% by weight; or such as 5% to 30%, 10% to 30%, 15% to 30%, or 20% to 30% by weight. In certain embodiments, the composition includes 5 to 10% by weight of the non-reducing sugar.

In some embodiments, the composition comprises 1% to 30% by weight of trehalose or a hydrate thereof, such as 1% to 25%, 1% to 20%, 1% to 15%, 1% to 10%, 2% to 10%, 3% to 10%, 4% to 10%, or 5% to 10% by weight; or such as 5% to 30%, 10% to 30%, 15% to 30%, or 20% to 30% by weight. In certain embodiments, the composition includes 5 to 10% by weight of trehalose or a hydrate thereof. In certain embodiments, the composition includes about 1% by weight of trehalose or a hydrate thereof. In certain embodiments, the composition includes about 1% by weight of trehalose or a hydrate thereof. In certain embodiments, the composition includes about 2% by weight of trehalose or a hydrate thereof. In certain embodiments, the composition includes about 3% by weight of trehalose or a hydrate thereof. In certain embodiments, the composition includes about 4% by weight of trehalose or a hydrate thereof. In certain embodiments, the composition includes about 5% by weight of trehalose or a hydrate thereof. In certain embodiments, the composition includes about 6% by weight of trehalose or a hydrate thereof. In certain embodiments, the composition includes about 7% by weight of trehalose or a hydrate thereof. In certain embodiments, the composition includes about 8% by weight of trehalose or a hydrate thereof. In certain embodiments, the composition includes about 9% by weight of trehalose or a hydrate thereof. In certain embodiments, the composition includes about 10% by weight of trehalose or a hydrate thereof.

Additional Components

The composition can include one or more additional components in addition to the non-reducing sugar component (e.g., an effective amount of the non-reducing sugar). In certain cases, the non-reducing sugar component is composed of particles of the sugar having a desirable median diameter (e.g., as described herein) suspended in an aqueous solution. In general, the one or more additional components include inert components (e.g., non-biologically active), non-polymeric components, and/or components which are biocompatible and biodegradable. Additional components of interest include, but are not limited to, buffering agents, salts (e.g., physiological saline), organic solvents, particle dispersion stabilizers or suspending agents, thickening agents, surfactants, pharmaceutically acceptable excipients or vehicles, carriers, and diluents (e.g., solutes that render the formulation isotonic with the bodily fluids of the intended recipient). Injectable formulations of the compositions can, in some embodiments, contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. Furthermore, physiologically-acceptable excipients can include, for example, 5% dextrose, 0.9% saline, Ringer's solution, Water-for-Injection, or 5% glucose solution.

In some instances, the composition includes a surfactant. As used herein, the term "surfactant" herein refers to organic substances having amphipathic structures; i.e., they are composed of groups of opposing solubility tendencies, in some cases an oil-soluble hydrocarbon chain and a water-soluble ionic group. Surfactants can be classified, depending on the surface-active moiety, into non-ionic, anionic, cationic and dispersing agents. In some cases, surfactants that find use with the subject compositions include, but are not limited to, non-ionic surfactants. Surfactants of interest include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); C10-C18 alkyl sulfates (e.g. sodium cetyl sulfate, sodium lauryl sulfate, sodium oleyl sulfate), polyoxyethylene C10-C18 alkyl ether sulfate with an average of 2 to 4 moles of ethylene oxide units added (e.g. sodium polyoxyethylene lauryl sulfate), and C1-C18 alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of C12-C18 fatty acids. A composition may include one or more of these surfactants. Preferred surfactants are polyoxyethylene sorbitan fatty acid esters e.g. polysorbate 20, 40, 60 or 80. In some case, Polysorbate 80 (Tween 80) is particularly useful. In some case, Polysorbate 20 (Tween 20) is particularly useful.

Buffering agents of interest for use with the subject compositions include, but are not limited to, organic acid salts such as salts of citric acid, ascorbic acid, gluconic acid, carbonic acid, tartaric acid, succinic acid, acetic acid or phtalic acid; Tris, tromethamine hydrochloride, or phosphate buffer. In addition, amino acid components can also be used as buffering agent. Such amino acid component includes without limitation glycine and histidine. In some cases, a histidine buffer is particularly useful. The subject aqueous compositions include such buffering agent or pH adjusting agent to provide improved pH control. In one embodiment, an aqueous pharmaceutical composition of the invention has a pH between 5.0 and 8.0, between 5.5 and 7.5, between 5.0 and 7.0, between 6.0 and 8.0, between 6.5 and 8.0, or between 7.0 and 8.0. In a specific embodiment, an aqueous composition of the invention has a pH of about 7.4. In a specific embodiment, an aqueous composition of the invention has a pH of about 7.5.

Other contemplated excipients, which may be utilized in the aqueous pharmaceutical compositions of the invention include, for example, flavoring agents, antimicrobial agents, bacteriostats, bactericidal antibiotics, antistatic agents, lipids such as phospholipids or fatty acids, steroids such as cholesterol, protein excipients such as serum albumin (human serum albumin), recombinant human albumin, gelatin, casein, salt-forming counterions such as sodium, and the like. These and additional pharmaceutical excipients and/or additives suitable for use in the subject compositions are known in the art, e.g., as listed in "The Handbook of Pharmaceutical Excipients, 4$^{th}$ edition, Rowe et al., Eds., American Pharmaceuticals Association (2003); and Remington: the Science and Practice of Pharmacy, 21th edition, Gennaro, Ed., Lippincott Williams & Wilkins (2005).

The composition may be an aqueous or a non-aqueous sterile suspension. Before a composition is administered to a subject it can be reconstituted with an aqueous reconstituent. This step permits components in the composition to re-dissolve or form a particulate suspension to give a solution which is suitable for injection to a subject. The volume of aqueous material used for reconstitution dictates the concentration of the non-reducing sugar in a resulting composition. The composition components can be reconstituted to give aqueous compositions with a non-reducing sugar concentration of at least 1% by weight, such as 1 to 30% by weight, 1 to 10% by weight or 5 to 10% by weight, and the volume of reconstituent will be selected accordingly. If required, the reconstituted composition can be diluted prior to administration to a subject as appropriate to deliver the intended amount of non-reducing sugar.

Reconstituents of interest (e.g., for lyophilised compositions) include sterile water or buffer, optionally containing a preservative. If the composition includes a buffering agent then the reconstituent may include further buffering agent (which may be the same as or different) or it may instead include no buffering agent (e.g. WFI (water for injection), or physiological saline).

As described above, aspects of the present disclosure include compositions which consist essentially of a non-reducing sugar component as the principle component. As such, the composition is generally devoid of additional active components, e.g., therapeutic agents such as antibodies or active proteins which specifically bind to a target, and polymeric components which provide structural features to the composition, such as a cross-linked polymer matrix.

In some cases, the subject compositions lack a gel or hydrogel component, or precursor thereof. In some cases, the subject compositions lack a polymeric component, e.g., a non-carbohydrate polymer. In some instances, the subject compositions lack a polymeric component, such as polyethylene glycol, hydroxymethylpropyl cellulose, chondroitin sulfate, polyacrylamide, collagen, dextran, heparin, agarose or chitosan. In some cases, the subject compositions lacks a polymerization initiator, or precursor thereof, such as 2-hydroxy-4'-(2-hydroxyethoxy)-2-methylpropiophenone, eosin Y, triethanolamine, or 1-vinyl-2-pyrrolidinone.

In certain instances, the subject compositions also lack a therapeutic agent or prodrug form thereof, such as an antibody, an oligonucleotide, a peptide or a small molecule drug. In certain cases, the composition is devoid of an antibody component. In certain cases, the composition is devoid of any protein component.

Methods

Aspects of the present disclosure include methods of preventing or reducing oxidative damage to an eye of a subject. In some cases, the damage is to the eye lens. In some embodiments, the method includes administering to the subject via intravitreal injection an ophthalmic composition (e.g., as described herein). The damage to the eye (e.g., to the eye lens) can occur as a result of vitreous removal or vitreous degeneration in the eye. In some embodiments, the method is a method of preventing or treating vitreous degeneration in the eye of a subject. The subject may be a subject at risk of vitreous degeneration (e.g., 50 years or older, such as 60 years or older or 70 years or older). In some cases, the method includes preventing or reducing the occurrence of oxidative damage in a subject. In some instances, the subject may already be experiencing vitreous degeneration and the method includes treating oxidative damage in the eye. In some cases, prior to the administrating step, the subject is assessed for vitreous degeneration. In some instances, the method includes replacing a portion of the vitreous humor of the subject. In some instances, the method includes adding the subject composition to the vitreous humor of the subject who is at risk of or experiencing vitreous degeneration.

The subject methods can also be performed on a subject in need of a vitrectomy, in conjunction with a vitrectomy procedure, or even post-vitrectomy. As such, in some instances, the method further includes surgical removal of at least a portion of the subject's vitreous humor during a vitrectomy. The subject compositions can be used to replace vitreous humor that is removed during a vitrectomy. In some embodiments of the method, reducing oxidative damage includes reducing cataract formation in the subject post-vitrectomy. Cataract formation, and the reduction thereof, can be assessed using any convenient methods, and at any convenient times, pre-, during or post-surgery.

With respect to the administration of the subject compositions to an eye of a subject to reduce an amount of oxidative damage, the terms "reduce," "reducing," or "reduction" when used herein in reference to oxidative damage are used to refer to any decrease or suppression in the amount or rate of oxidative damage to the tissue of a subject, such as the eye lens. Any convenient methods of assessing oxidative damage can be utilized, including quantitative or qualitative methods, such as methods that include measuring the amount of oxidation of a protein in a biological sample, or methods involving visualizing opacity in the eye. Of course, it is understood that the degree of reduction need not be absolute (i.e., the degree of inhibition need not be a complete prevention of oxidative damage) and that intermediate levels of a reduction in oxidative damage are contemplated by the presently-disclosed subject matter. As such, in some embodiments, the reduction in oxidative damage can be about 5% or more, such as about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more, e.g., as measured relative to any convenient control (e.g., as described herein, see e.g., FIG. 1).

In certain embodiments, the subject method provides for reducing oxidative damage in the eye by 10% or more as compared to a control composition including a biogel, such as by 15% or more, 20% or more, 25% or more, 30% or more, 35% or more, 40% or more, 45% or more, 50% or more, or even more, e.g., as measured using any convenient protein oxidation assay. In certain embodiments, the subject method provides for reducing oxidative damage in the eye by 10% or more as compared to a control composition that is coated on the eye lens, such as by 15% or more, 20% or more, 25% or more, 30% or more, 35% or more, 40% or more, 45% or more, 50% or more, or even more, e.g., as measured using any convenient protein oxidation assay. In certain instances, the oxidative damage in the eye is reduced by 40% or more as compared to a control composition that is coated on the eye lens. In certain embodiments, the subject method provides for reducing lens protein oxidation in the eye to a reduced level of 40% or less, such as a level of 35% or less, a level of 30% or less, a level of 25% or less, a level of 20% or less, a level of 15% or less, a level of 10% or less, or even less e.g., as measured relative to a control using any convenient assay of protein oxidation. FIG. 1 illustrates the reduced levels of protein oxidation that were achieved by an exemplary composition of the present disclosure.

In some embodiments, the method includes reducing the occurrence of opacity or cataracts in the eye, e.g., as assessed relative to any convenient control. In certain embodiments, the occurrence of a cataract is assessed by slit-lamp examination, or by a visual acuity measurement. In some instances, reduction in the occurrence of opacity or cataracts in the eye that is achieved in the subject methods is assessed by measuring a period of time post-surgery in which no opacity is observed in the eye. In some cases, the subject methods prevent or delay the onset of opacity or cataracts in the eye for at least 1 week, such as at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 1 year, at least 2 years, at least 5 years, at least 10 years, or even indefinitely.

For administration of a composition as disclosed herein, in some embodiments, the presently-described compositions can be administered to a subject using a variety of different applicators including needles, plastic, ceramic, or metal applicators, and the like. For example, in some embodiments, an exemplary composition is administered to a subject by directly injecting the antioxidant composition through a small bore needle, such as a 25 or 27 gauge needle, into the vitreous humor of an eye of a subject. In some embodiments, the composition is administered to a subject by directly injecting the antioxidant composition through a needle, such as a needle having a gauge in the range of 28 to 30 (e.g., 28, 29 or 30 gauge), into the vitreous humor of an eye of a subject. In some embodiments, when the composition is administered to the vitreous humor, the composition can be administered in close proximity to, but without contacting, the eye lens of the subject. In certain embodiments, the subject is a mammal. In certain embodiments, the subject is human.

Regardless of the particular mode of administration used in accordance with the methods of the presently-disclosed subject matter, the antioxidant compositions described herein can be administered in an amount effective to achieve the desired response (e.g., a reduction in oxidative damage). As such, the term "effective amount" is used herein to refer to an amount of the therapeutic composition (e.g., an antioxidant composition including a non-reducing sugar) sufficient to produce a measurable biological response (e.g., a reduction in oxidative damage or the occurrence of cataracts). Actual dosage levels of active ingredient in an ophthalmic composition of the presently-disclosed subject matter (e.g., the non-reducing sugar(s)) can be varied so as to administer an amount of the composition that is effective to achieve the desired therapeutic response for a particular subject and/or application. The selected dosage level and amount of the non-reducing sugar(s) and the other components of the composition will depend upon a variety of factors including the activity of the non-reducing sugar(s), formulation, the route of administration, combination with other drugs or treatments, severity of the condition being treated, and the physical condition and prior medical history of the subject being treated. In some cases, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

In some instances, after administration, the particles of the non-reducing sugar dissolve in situ at a rate sufficient to provide for an effective intravitreal concentration of trehalose over an extended period of time. In certain embodiments, the extended period of time is 1 day or more, such as 2 days or more, 3 days or more, 4 days or more, 5 days or more, 6 days or more, 1 week or more, 2 weeks or more, 3 weeks or more, 1 month or more, 2 months or more, 3 months or more, 6 months or more, 12 months or more, or even more. In certain embodiments, the extended period of time is 1 day or more. In certain embodiments, the extended period of time is 1 week or more. In certain embodiments, the extended period of time is 1 month or more. In certain embodiments, the extended period of time is 3 months or more.

Administration of the subject composition may be performed at any convenient time in conjunction with a vitrectomy. The composition can be administered separately but sufficiently closely in time to the vitrectomy so as to provide the desired therapeutic effect. A vitrectomy can include surgical removal of a portion of a subject's vitreous humor. In some instances, the administering is performed prior to the surgical removal. In some instances, the administering is performed during the surgical removal. In some instances, the administering is performed after the surgical removal.

In certain instances, during the vitrectomy procedure sufficient intraocular pressure is maintained in the subject to prevent retinal detachment. A variety of steps can be performed in order to maintain sufficient intraocular pressure. In certain instances, during a vitrectomy procedure an infusion of fluid is used to maintain sufficient intraocular pressure. In some cases, the fluid infusion includes a gas, such as $SF_6$, $N_2$ or air. In certain cases, the fluid infusion includes a liquid. In certain cases, the fluid infusion includes a mixture of liquid and gas. The subject ophthalmic compositions can be administered with (e.g., as part of) the fluid infusion step of a vitrectomy.

Pre-Loaded Injection Device

Aspects of the present disclosure include an injection device suitable for administration of the composition that is pre-loaded with the subject composition (e.g., as described herein). By pre-loaded is meant that the device contains (e.g., in a reservoir) a composition for injection into a subject. In some cases, the injection device is empty, but suitable for loading, and can be included in a kit containing the subject composition. In some instances, the device is pre-loaded with a unit dosage of the subject composition. As used herein, a "unit dosage" is an amount suitable for administration at one time. The unit dosage can provide an effective amount of the non-reducing sugar. In some instances, the device includes the composition disposed therein in a dry or lyophilized form that requires reconstitution prior to use. In some cases, a fluid reservoir, optionally pre-loaded with a diluent for reconstituting the composition is included with the device. Any convenient injection devices, or components thereof, that find use in intravitreal injections may be adapted for use in the subject devices. In some embodiment, the injection device includes means for intravitreal injection. For example, means for intravitreal injection may include a syringe. Any convenient syringes may be utilized. The syringe may be disposable. In general, the syringe includes a chamber or reservoir (e.g., a barrel) in which the composition can be contained (e.g., in dry form for reconstitution or in a form ready for administration), and a needle assembly operably connected to the chamber or reservoir. In one embodiment, the subject composition has a injectability for intravitreal administration to an eye of a subject. For example, the composition, when disposed in a syringe suitable for intravitreal delivery can be expelled and thereby injected into a site of the subject in the eye, using pressure sufficient to depress a plunger.

The device can include a needle suitable for injecting into the vitreous humor of an eye of a subject. In some cases, the device includes a small bore needle, such as a 25, 26 or 27 gauge needle. In certain cases, the needle gauge is 25. In certain cases, the needle gauge is 26. In certain cases, the needle gauge is 27. In some embodiments, the device includes a needle having a gauge in the range of 28 to 30 (e.g., a 28, 29 or 30 gauge). In certain cases, the needle gauge is 28. In certain cases, the needle gauge is 29. In certain cases, the needle gauge is 30. In some instances, the device is a pre-loaded syringe assembly with a plurality of sterility barriers. The pre-loaded syringe assemblies can include a plurality of sterility barriers to maintain the sterility of certain components of the syringe assemblies during packaging, shipping and storage until use by a medical professional. The pre-loaded syringe assemblies disclosed herein can be shipped to a medical professional in a pre-armed state while maintaining sterility of the contents, e.g., a pre-loaded cartridge and the surfaces of components that will come into contact with the contents of the cartridge. In some cases, prior to use of the pre-loaded syringe assemblies disclosed herein, a medical professional places the assembly in an armed state by forming a sterile fluid pathway between a needle tip and the contents of the cartridge. Placement of the assembly into the armed state can occur by placing pressure on a terminal end of a plunger to move the cartridge toward a distal end of the assembly and cause a butt end of the needle to pierce a septum attached to the cartridge. During such arming, the cartridge and the plunger move distally relative to a fixed housing. Injection devices of interest which may be adapted for use with the subject compositions include, but are not limited to, those described in US 20150073353, US 20110213380, U.S. Pat. Nos. 5,643,276, 7,892,282, US 20150290078 and US 20150366708, the disclosures of which are herein incorporated by reference.

In one embodiment, activating the device comprises one of more of removing the device from a packaging, removing a cover from a needle or orifice of the device, or shaking the device. In another embodiment, activating the device further includes inspecting the device for the presence of suspension, precipitate, colored material, or turbidity, or opalescence.

In some embodiments, the device (e.g., a pre-loaded syringe) includes an ophthalmic composition (e.g., as described herein), such as a composition consisting essentially of: 1% to 30% by weight of an aqueous suspension of particles of a non-reducing sugar (e.g., trehalose or a hydrate thereof). In certain embodiments of the device, the particles have an mean diameter in the range of 100 to 2000 nm (e.g., as described herein). In certain embodiments of the device, the composition comprises a non-ionic surfactant. In certain embodiments of the device, the composition comprises a sterile biocompatible buffer. Any of the non-reducing sugars and compositions thereof described herein can be pre-loaded into the subject device. In certain embodiments of the device, the non-reducing sugar is trehalose.

Kits

Aspects of the present disclosure further include kits that find use in practicing the subject methods. In some embodiments, the kits for practicing the subject methods include one or more ophthalmic compositions, which include one or more non-reducing sugars, e.g., as described herein. As such, in certain embodiments the kits may include a single ophthalmic composition, present as one or more unit dosages.

Any of the components described herein may b e provided in the kits. A variety of components suitable for use in practicing the subject methods may find use in the subject kits. Kits may also include one or more components including, but not limited to, means for intraocular (e.g., intravitreal) injection (e.g., an injection device suitable for intravitreal injection), an eye numbing agent, a sterile dilution buffer, a trocar device, means for measuring intraocular pressure, a sealed package configured to maintain the sterility of the ophthalmic pharmaceutical composition, sterile containers, pharmaceutically acceptable solutions, freeze-dried solids thereof, tubes, buffers, etc., and instructions for use.

The ophthalmic composition can be pre-loaded into an injection device (e.g., a syringe) suitable for intravitreal injection, or can be included in the kit as a separate component. In certain instances, the ophthalmic composition included in the kit consists essentially of: 1% to 30% by weight of an aqueous suspension of particles of a non-reducing sugar or a hydrate thereof (e.g., trehalose), wherein the particles have an mean diameter in the range of 100 to 2000 nm (e.g., as described herein). In certain embodiments of the kit, the composition comprises a non-ionic surfactant. In certain embodiments of the kit, the composition comprises a sterile biocompatible buffer. Any of the non-reducing sugars and compositions thereof described herein can be utilized. In certain embodiments of the kit, the non-reducing sugar is trehalose.

The various components of the kits may be present in separate containers, or some or all of them may be pre-combined into a mixture in a single container, as desired. In certain embodiments, the kit includes a sterile container containing a pharmaceutically acceptable solution of the subject composition; and an optionally sealed package configured to maintain the sterility of the sterile container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), hard drive etc., on which the information has been recorded. Yet another form of these instructions that may be present is a website address which may be used via the internet to access the information at a removed site. For example, a kit according to one embodiment includes as a first component (a) instructions for using a pharmaceutical composition, and as a second component (b) an ophthalmic composition comprising the non-reducing sugar.

Utility

The methods, compositions, devices and kits of the present disclosure, e.g., as described herein, find use in a variety of applications. Applications of interest include, but are not limited to: research applications and therapeutic applications. The subject methods compositions, devices and kits may be employed in the treatment of a variety of eye diseases or conditions, including but not limited to, any disease or condition involving oxidative stress or damage to the eye. Eye diseases of interest include, but are not limited to, age-related vitreous degeneration, cataracts, conditions involving risk or occurrence of retinal detachment, macular pucker, diabetic retinopathy, macular holes, vitreous hemorrhage and/or vitreous floaters, and conditions such as diabetic eye disease.

In some embodiments, the subject methods are employed in the treatment of subjects in need of vitrectomy, e.g., to prevent or reduce the occurrence of cloudiness or cataracts in the eye lens of a patient. Vitrectomy is surgery to remove some or all of the vitreous humor from the eye. Vitrectomy surgeries where the subject methods, compositions, devices and kits find use include, but are not limited to, anterior vitrectomy, pars plana vitrectomy. In some embodiments, the methods and compositions find use in conjunction with corneal transplantation, e.g., low risk or high risk (of rejection) corneal transplantation.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

To assess the ability of the antioxidant compositions including non-reducing sugars to reduce oxidative damage to an eye lens of a subject, trehalose, a non-reducing disaccharide, was applied to lenses being cultured under hyperoxic (high oxygen) conditions that mimic post-vitrectomy intravitreal oxygen levels. Briefly, six excised porcine lenses were cultured in M199 media with 4% porcine serum at 37° C. for 1 week to acclimate to culture conditions. Then, 3 lenses were exposed to media with 7.5% trehalose while three control lenses remained untreated. At regular intervals, incubated lenses were examined under a dissecting microscope against a background of black gridlines. The oxygen concentration was controlled to mimic post-vitrectomy conditions. After 10 days, each lens was analyzed for protein oxidation using the OxBlot Oxidized Protein Detection Kit (Chemicon, International, Billerica, MA) to quantify the ability of the gel application method to protect the lens.

The method described above was used to compare the effect of a subject trehalose composition freely dispersed in the tissue culture media (FIG. 1, first bar) to a biogel composition that was described by Tezel et al. in WO2014081969A1 ("Compositions and methods for reducing oxidative damage") and which includes trehalose within a polymer gel. The Biogel composition was either applied next to, but not in contact with, the lens (FIG. 1, second bar), or was applied directly as a coating on the lens (FIG. 1, third bar). As shown in FIG. 1, upon analysis of the results from the experiments, it was observed that administration of trehalose to the eye lens reduced an amount of protein oxidation in the lens. The uncoated biogel composition resulted in a reduction in protein oxidation to approximately 30% versus an approximately reduction to 70% with the coated biogel composition. The subject trehalose composition (FIG. 1, bar 1) resulted in an even greater reduction in protein oxidation levels to about 20%.

These results thus indicate that trehalose and other non-reducing sugars are useful in protecting an eye lens from oxidative damage. The results further indicate that coating of the eye lens is not necessary to achieve the levels of protection.

Example 2

Figure 2:
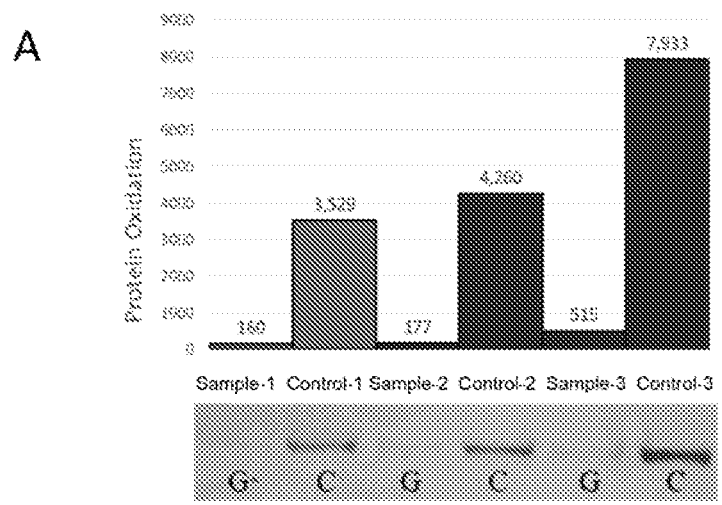
FIG. 2, panels A-C, illustrate that administration of trehalose-containing compositions to the eye lens in an in vivo model resulted in a reduced an amount of protein oxidation in the lens post-vitrectomy. Panel A shows the results obtained for three replicate experiments in porcine eyes using a lens coated Trehalose biogel composition.
Figure 2:
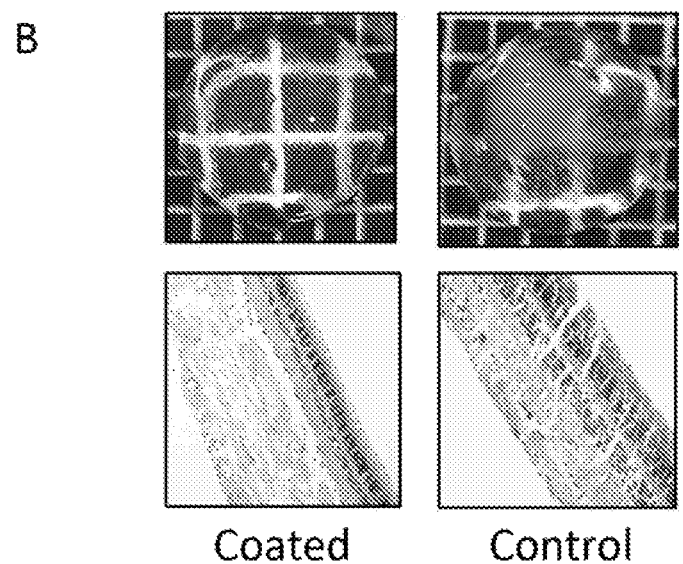
Figure 2:
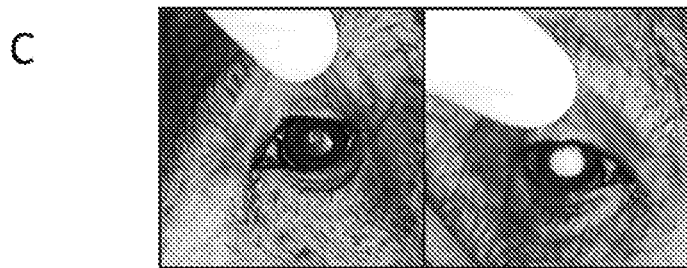

FIG. 2, panels A-C, illustrates that administration of trehalose-containing compositions to the eye lens in an in vivo model resulted in a reduced an amount of protein oxidation in the lens. To test in vivo applicability and safety of antioxidant formulations to prevent oxidative damage of the crystalline lens after vitrectomy in vivo experiments were conducted on pig eyes. Intraoperative applicability, safety and efficacy of the product to prevent cataract formation following vitrectomy was tested in-vivo using 17 seven-month-old domestic porcine (Sus domestica) eyes.

In a first experiment, a composition that was described by Tezel et al. in WO2014081969A1 ("Compositions and methods for reducing oxidative damage") and which includes trehalose was used for in vivo testing. For this purpose, 3 port 25 G pars plana vitrectomies were performed, and 150 J . . . LL of formula was injected in close proximity of the posterior surface of the lens using a 25G needle as an applicator. An untreated but vitrectomized fellow eye was taken as control. Following surgery, ocular exams were done on post-operative days 0, 1, 7, 28, 60, 90 & 180. Electroretinogram (ERG) of the each eye was also obtained and compared before and after the surgery. The clinical eye exam consisted of slit-lamp examination for LOCS III grading of cataract progression and indirect ophthalmoscopy, tonometry, and color fundus photographs. At pre-determined time points of 1, 3, and 6 months animals were euthanized and lenses were recovered to grade the lens opacity by determining the clarity of a background Amsler grid with ImageJ software and also to extract the lens proteins to assess the amount of protein oxidation (OxyBlot Oxidized Protein Detection Kit, Chemicon, International, Billerica, MA). Formulated bio-gel successfully prevented cataract formation in 13 of 17 (64%) eyes following vitrectomy surgery. Four of 17 (23%) treatment eyes suffered iatrogenic cataract formation due to the inadvertent lens trauma during surgery. Western blot revealed a greater degree of protein oxidation in the control (vs. treated) samples, FIG. 2, panel A. No inflammation, IOP increase, lens dislocation or harmful adverse effects were noted during the clinical and electrophysiological exam, FIG. 2, panel B. Significantly increased "Visibility Scores" were attained in eyes where the lens was treated with our formulation, FIG. 2, panel C. These in vivo studies reveal the formulation is biocompatible, non-immunogenic, and well tolerated. No acute toxicity, pressure increases, or other adverse effects were detected in association with the product. Current application methods are simple and reproducible, and the porcine surgical model has shown promising results revealing that the product can prevent oxygen-induced cataract formation after vitrectomy surgery.

These in vivo experiments and the experiments comparing the activity of an exemplary composition of the present disclosure with the biogel composition of Tezel et al. demonstrate that formulations containing trehalose particles are effective in preventing oxidative damage to the lens and preventing cataracts while causing no toxic or otherwise adverse side effects.

EMBODIMENTS

Aspects of the present disclosure include a method of reducing oxidative damage to an eye of a subject. In some embodiments, the method comprises administering an effective amount of an antioxidant composition including a non-reducing sugar to the eye of the subject. In some embodiments, the non-reducing sugar is a disaccharide. In certain embodiments, the disaccharide is trehalose. In some embodiments, the antioxidant composition is in the form of a biocompatible hydrogel. In some embodiments, the administering the antioxidant composition comprises administering the antioxidant composition to a vitreous humor of the eye of the subject. In some embodiments, the step of administering the composition comprises injecting the composition through a needle into the vitreous humor of the subject. In some embodiments, the antioxidant is included in the composition at a concentration of about 5 wt % to about 10 wt %. In some embodiments, the antioxidant is included in the composition as a plurality of antioxidant particles. In some embodiments of the method, the antioxidant particles have a diameter of about 50 nm to about 1000 nm.

Aspects of the present disclosure include methods of preventing or reducing oxidative damage to an eye of a subject. In some embodiments, the method comprises administering to the subject via intravitreal injection an ophthalmic composition consisting essentially of a non-reducing sugar or a hydrate thereof. In certain embodiments, the subject method provides for reducing oxidative damage in the eye by 10% or more as compared to a control composition including a biogel, such as by 15% or more, 20% or more, 25% or more, 30% or more, 35% or more, 40% or more, 45% or more, 50% or more, or even more, e.g., as measured using any convenient protein oxidation assay. In certain embodiments, the subject method provides for reducing oxidative damage in the eye by 10% or more as compared to a control composition that is coated on the eye lens, such as by 15% or more, 20% or more, 25% or more, 30% or more, 35% or more, 40% or more, 45% or more, 50% or more, or even more, e.g., as measured using any convenient protein oxidation assay. In some embodiments, the method is a method of preventing or treating vitreous degeneration in the eye of a subject. In some instances, the method includes replacing a portion of the vitreous humor of the subject. In some instances, the method includes adding the subject composition to the vitreous humor of the subject who is at risk of or experiencing vitreous degeneration.

Embodiment 1. A method of reducing oxidative damage to an eye of a subject, the method comprising administering to the subject via intravitreal injection an ophthalmic composition consisting essentially of a non-reducing sugar or a hydrate thereof.

Embodiment 2. The method of embodiment 1, further comprising surgical removal of at least a portion of the subject's vitreous humor during a vitrectomy.

Embodiment 3. The method of embodiment 2, wherein the administering is performed prior to the surgical removal.

Embodiment 4. The method of embodiment 2, wherein the administering is performed after the surgical removal.

Embodiment 5. The method of any one of embodiments 1-4, wherein the vitrectomy comprises maintaining sufficient intraocular pressure to prevent retinal detachment.

Embodiment 6. The method of embodiment 5, wherein maintaining sufficient intraocular pressure includes infusion of a fluid.

Embodiment 7. The method of embodiment 6, wherein the ophthalmic composition is administered with the fluid infusion.

Embodiment 8. The method of any one of embodiments 1-7, wherein the composition comprises a particulate suspension of the non-reducing sugar or hydrate thereof.

Embodiment 9. The method of embodiment 8, wherein the particles have a mean diameter sufficient to prevent passage through pores in the ciliary body of the eye.

Embodiment 10. The method of any one of embodiments 1-9, wherein the non-reducing sugar is a trehalose oligosaccharide.

Embodiment 11. The method of any one of embodiments 1-10, wherein the non-reducing sugar is a disaccharide.

Embodiment 12. The method of any one of embodiments 1-10, wherein the non-reducing sugar is trehalose.

Embodiment 13. The method of any one of embodiments 1-9, wherein the non-reducing sugar is a sucrose oligosaccharide.

Embodiment 14. The method of any one of embodiments 1-9 and 13, wherein the non-reducing sugar is sucrose.

Embodiment 15. The method of any one of embodiments 1-15, wherein the non-reducing sugar is present in the composition as a particulate having a mean diameter in the range of 100 to 2000 nm.

Embodiment 16. The method of any one of embodiments 1-15, wherein the non-reducing sugar is present in the composition as a particulate having a median diameter of 600±200 nm.

Embodiment 17. The method of any one of embodiments 1-16, wherein the composition comprises 1% to 30% by weight of the non-reducing sugar.

Embodiment 18. The method of any one of embodiments 1-17, wherein the composition comprises 5% to 10% by weight of the non-reducing sugar.

Embodiment 19. The method of any one of embodiments 1-18, wherein reducing oxidative damage comprises reducing post-vitrectomy cataract formation in the subject.

Embodiment 20. The method of any one of embodiments 8-9, 15 and 16, wherein the particles of the non-reducing sugar dissolve at a rate sufficient to provide for an effective intravitreal concentration of trehalose over an extended period of time.

Embodiment 21. The method of embodiment 20, wherein the extended period of time is 1 day or more.

Embodiment 22. The method of embodiment 20 or 21, wherein the extended period of time is 1 week or more.

Embodiment 23. The method of any one of embodiments 20-22, wherein the extended period of time is 1 month or more.

Embodiment 24. The method of any one of embodiments 20-23, wherein the non-reducing sugar is trehalose or a hydrate thereof.

Embodiment 25. The method of any one of embodiments 1-24, wherein the composition consists essentially of: a particulate suspension of an effective amount of trehalose or a hydrate thereof in an aqueous solution; a buffering agent; and an optional non-ionic surfactant.

Embodiment 26. The method of embodiment 25, wherein the non-ionic surfactant is polysorbate 20.

Embodiment 27. A pre-loaded injection device for use in vitrectomy surgery, comprising: a means for intravitreal injection; and an ophthalmic composition consisting essentially of a non-reducing sugar or a hydrate thereof.

Embodiment 28. The pre-loaded injection device of embodiment 27, wherein the device is a syringe.

Embodiment 29. The pre-loaded injection device of embodiment 27 or 28, wherein the means for intravitreal injection comprises a needle having a gauge suitable for intravitreal injection.

Embodiment 30. The pre-loaded injection device of embodiment 29, wherein the needle has a gauge in the range of 28 to 30.

Embodiment 31. The pre-loaded injection device of any one of embodiments 27-30, wherein the device contains one unit dosage of the ophthalmic composition.

Embodiment 32. The pre-loaded injection device of any one of embodiments 27-31, wherein the ophthalmic composition requires reconstitution in a pharmaceutically acceptable diluent prior to administration.

Embodiment 33. The pre-loaded injection device of embodiment 32, wherein the device further comprises a fluid reservoir pre-loaded with a diluent for reconstituting the ophthalmic composition.

Embodiment 34. The pre-loaded injection device of any one of embodiments 27-33, wherein the composition comprises a particulate suspension of the non-reducing sugar or hydrate thereof.

Embodiment 35. The pre-loaded injection device of embodiment 34, wherein the particles have a mean diameter sufficient to prevent passage through pores in the ciliary body of an eye.

Embodiment 36. The pre-loaded injection device of any one of embodiments 27-35, wherein the non-reducing sugar is a trehalose oligosaccharide.

Embodiment 37. The pre-loaded injection device of any one of embodiments 27-36, wherein the non-reducing sugar is a disaccharide.

Embodiment 37b. The pre-loaded injection device of any one of embodiments 27-36, wherein the non-reducing sugar is trehalose.

Embodiment 38. The pre-loaded injection device of any one of embodiments 27-35, wherein the non-reducing sugar is a sucrose oligosaccharide.

Embodiment 39. The pre-loaded injection device of any one of embodiments 27-35 and 38, wherein the non-reducing sugar is sucrose.

Embodiment 40. The pre-loaded injection device of any one of embodiments 27-39, wherein the non-reducing sugar is present in the composition as a particulate having a mean diameter in the range of 100 to 2000 nm.

Embodiment 41. The pre-loaded injection device of any one of embodiments 27-40, wherein the non-reducing sugar is present in the composition as a particulate having a median diameter of 600±200 nm.

Embodiment 42. The pre-loaded injection device of any one of embodiments 27-41, wherein the composition comprises 1% to 30% by weight of the non-reducing sugar.

Embodiment 43. The pre-loaded injection device of any one of embodiments 27-42, wherein the composition comprises 5% to 10% by weight of the non-reducing sugar.

Embodiment 44. The pre-loaded injection device of any one of embodiments 27-43, wherein the composition consists essentially of: a particulate suspension of an effective amount of trehalose or a hydrate thereof in an aqueous solution; a buffering agent; and an optional non-ionic surfactant.

Embodiment 45. The pre-loaded injection device of embodiment 44, wherein the non-ionic surfactant is polysorbate 20.

Embodiment 46. The pre-loaded syringe of any one of embodiments 27-45, wherein the ophthalmic composition, consists essentially of: 1% to 30% by weight of an aqueous suspension of particles of a non-reducing sugar or a hydrate thereof, wherein the particles have an mean diameter in the range of 100 to 2000 nm.

Embodiment 47. The pre-loaded syringe of embodiment 46, wherein the composition comprises a non-ionic surfactant.

Embodiment 48. The pre-loaded syringe of embodiment 46, wherein the composition comprises a sterile biocompatible buffer.

Embodiment 49. The pre-loaded syringe of any one of embodiments 27-48, wherein the non-reducing sugar is trehalose or a hydrate thereof.

Embodiment 50. A kit, comprising: an ophthalmic composition consisting essentially of a non-reducing sugar; and one or more components selected from an eye numbing agent, a sterile dilution buffer, means for intravitreal injection, a trocar device, means for measuring intraocular pressure and instructions for use.

Embodiment 51. The kit of embodiment 50, wherein the ophthalmic composition is pre-loaded into an injection device suitable for intravitreal injection.

Embodiment 52. The kit of embodiment 50, wherein the kit comprises a pre-loaded injection device according to any one of embodiments 28-49.

Embodiment 53. The kit of embodiment 50, wherein the composition comprises a particulate suspension of the non-reducing sugar or hydrate thereof.

Embodiment 54. The kit of embodiment 53, wherein the particles have a mean diameter sufficient to prevent passage through pores in the ciliary body of an eye.

Embodiment 55. The kit of any one of embodiments 50-54, wherein the non-reducing sugar is a trehalose oligosaccharide.

Embodiment 56. The kit of any one of embodiments 50-55, wherein the non-reducing sugar is a disaccharide.

Embodiment 57. The kit of any one of embodiments 50-55, wherein the non-reducing sugar is trehalose.

Embodiment 58. The kit of any one of embodiments 50-54, wherein the non-reducing sugar is a sucrose oligosaccharide.

Embodiment 59. The kit of any one of embodiments 50-54 and 58 wherein the non-reducing sugar is sucrose.

Embodiment 60. The kit of any one of embodiments 50-59, wherein the non-reducing sugar is present in the composition as a particulate having a mean diameter in the range of 100 to 2000 nm.

Embodiment 61. The pre-loaded injection device of any one of embodiments 50-60, wherein the non-reducing sugar is present in the composition as a particulate having a median diameter of 600±200 nm.

Embodiment 62. The kit of any one of embodiments 50-61, wherein the composition comprises 1% to 30% by weight of the non-reducing sugar.

Embodiment 63. The kit of any one of embodiments 50-62, wherein the composition comprises 5% to 10% by weight of the non-reducing sugar.

Embodiment 64. The kit of any one of embodiments 50-63, wherein the composition consists essentially of: a particulate suspension of an effective amount of trehalose or a hydrate thereof in an aqueous solution; a buffering agent; and an optional non-ionic surfactant.

Embodiment 65. The kit of embodiment 64, wherein the non-ionic surfactant is polysorbate 20.

Embodiment 66. The kit of any one of embodiments 50-65, wherein the ophthalmic composition, consists essentially of: 1% to 30% by weight of an aqueous suspension of particles of a non-reducing sugar or a hydrate thereof, wherein the particles have an mean diameter in the range of 100 to 2000 nm.

Embodiment 67. The kit of embodiment 66, wherein the composition comprises a non-ionic surfactant.

Embodiment 68. The kit of embodiment 46, wherein the composition comprises a sterile biocompatible buffer.

Embodiment 69. The kit of any one of embodiments 50-68, wherein the non-reducing sugar is trehalose or a hydrate thereof.

Embodiment 70. An ophthalmic composition, consisting essentially of: 1% to 30% by weight of an aqueous suspension of particles of a non-reducing sugar or a hydrate thereof, wherein the particles have an mean diameter in the range of 100 to 2000 nm.

Embodiment 71. The ophthalmic composition of embodiment 70, wherein the particles have a mean diameter sufficient to prevent passage through pores in the ciliary body of an eye.

Embodiment 72. The ophthalmic composition of any one of embodiments 70-71, wherein the non-reducing sugar is a trehalose oligosaccharide.

Embodiment 73. The ophthalmic composition of any one of embodiments 70-72, wherein the non-reducing sugar is a disaccharide.

Embodiment 74. The ophthalmic composition of any one of embodiments 70-72, wherein the non-reducing sugar is trehalose.

Embodiment 75. The ophthalmic composition of any one of embodiments 70-74, wherein the non-reducing sugar is a sucrose oligosaccharide.

Embodiment 76. The ophthalmic composition of any one of embodiments 70, 71 and 75, wherein the non-reducing sugar is sucrose.

Embodiment 77. The ophthalmic composition of any one of embodiments 70-76, wherein the composition comprises a non-ionic surfactant.

Embodiment 78. The ophthalmic composition of any one of embodiments 70-77, wherein the composition comprises a sterile biocompatible buffer.

Embodiment 79. The ophthalmic composition of any one of embodiments 70-78, wherein the non-reducing sugar is present in the composition as a particulate having a median diameter of 600±200 nm.

Embodiment 80. The ophthalmic composition of any one of embodiments 70-79, wherein the composition comprises 5% to 10% by weight of the non-reducing sugar.

Embodiment 81. The ophthalmic composition of any one of embodiments 70-80, wherein the composition consists essentially of: a particulate suspension of an effective amount of trehalose or a hydrate thereof in an aqueous solution; a buffering agent; and an optional non-ionic surfactant.

Embodiment 81. The ophthalmic composition of embodiment 81, wherein the non-ionic surfactant is polysorbate 20.

Embodiment 82. The ophthalmic composition of any one of embodiments 77-81, wherein the non-reducing sugar is trehalose or a hydrate thereof.

Embodiment 83. The use of a non-reducing sugar (e.g., as described herein) in the manufacture of a medicament for use in methods of any one of embodiments 1 to 26.

Embodiment 84. The use of an ophthalmic composition comprising a non-reducing sugar (e.g., as described herein) in the manufacture of a medicament for use in methods of any one of embodiments 1 to 26.

Embodiment 85. An ophthalmic composition (e.g., as described herein) for use in the methods of any one of embodiments 1 to 26.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing oxidative damage to an eye of a subject, the method comprising administering to the subject via intravitreal injection an ophthalmic composition consisting essentially of a non-reducing sugar or a hydrate thereof.

2. The method of claim 1, further comprising surgical removal of at least a portion of the subject's vitreous humor during a vitrectomy.

3. The method of claim 2, wherein the vitrectomy comprises maintaining sufficient intraocular pressure to prevent retinal detachment by infusion of a fluid.

4. The method of claim 3, wherein the ophthalmic composition is administered with the fluid infusion.

5. The method of claim 1, wherein the non-reducing sugar is present in the composition as a particulate having a mean diameter in the range of 100 to 2000 nm.

6. The method of claim 1, wherein the composition comprises 1% to 30% by weight of the non-reducing sugar.

7. The method of claim 2, wherein reducing oxidative damage comprises reducing post-vitrectomy cataract formation in the subject.

8. The method of claim 1, wherein the composition consists essentially of:
   a particulate suspension of an effective amount of trehalose or a hydrate thereof in an aqueous solution;
   a buffering agent; and
   an optional non-ionic surfactant.

* * * * *